United States Patent [19]
Malone et al.

[11] Patent Number: 6,110,898
[45] Date of Patent: Aug. 29, 2000

[54] DNA VACCINES FOR ELICITING A MUCOSAL IMMUNE RESPONSE

[75] Inventors: Robert W. Malone; Jill G. Malone, both of Baltimore, Md.

[73] Assignee: University of Maryland, Baltimore, Baltimore, Md.

[21] Appl. No.: 08/862,632

[22] Filed: May 23, 1997

Related U.S. Application Data

[60] Provisional application No. 60/018,269, May 24, 1996.

[51] Int. Cl.$^7$ .......................... A61K 48/00; C17N 15/00; C12Q 1/70
[52] U.S. Cl. .............................. 514/44; 435/6; 435/69.1; 435/91.1; 435/455; 424/93.1; 424/204.1; 424/234.1; 424/256.1
[58] Field of Search .......................... 435/6, 69.1, 172.3, 435/325, 320.1, 91.1, 455; 536/23.1; 514/44; 424/93.1, 204.1, 234.1, 256.1

[56] References Cited

U.S. PATENT DOCUMENTS

| | | | |
|---|---|---|---|
| 5,589,466 | 12/1996 | Felgner et al. | 514/44 |
| 5,593,972 | 1/1997 | Weiner et al. | |
| 5,703,055 | 12/1997 | Felgner et al. | 514/14 |

FOREIGN PATENT DOCUMENTS

| | | |
|---|---|---|
| WO 97/11605 | 9/1996 | WIPO . |
| WO 97/14442 | 10/1996 | WIPO . |
| WO 97/31119 | 2/1997 | WIPO . |
| WO 98/40499 | 3/1997 | WIPO . |
| WO 98/04720 | 7/1997 | WIPO . |
| WO 98/48026 | 12/1997 | WIPO . |
| WO 98/48626 | 4/1998 | WIPO . |

OTHER PUBLICATIONS

Kiyono, H., et al. "The Common Mucosal Immune System for the Reproductive Tract: Basic Principles Applied toward an AIDS Vaccine" *Adv. Drug Del. Rev.* 18:23–51, 1995.

Miller, C.J., et al. "Rhesus Macaques Previously Infected with Simian/Human Immunodeficiency Virus Are Protected from Vaginal Challenge with Pathogenic SIVmac239" *J. Virol.* 71:1911–1921, 1997.

Gallichan, W. S., et al. "Mucosal Immunization with a Recombinant Adenovirus Vector Induces Local and Systemic Immunity and Protection from Herpes Simplex Virus" *Adv. in Mucosal Immun.* 1581–1585, 1995.

Anderson, M.J., et al. "Characterization of the Expression and Immunogenicity of Poliovirus Replicons that Encode Simian Immunodeficiency Virus $SIV_{mac}239$ Gag or Envelope SU Proteins" *AIDS Res. Hum Retroviruses* 13:53–62, 1997.

Sabbaj, S., et al. "Mucosal Immunisation for Enteric Diseases" *BioDrugs*, 2:134–157, Adis International Ltd., 1997.

Bassler, K.D., et al. "Genetic Immunization: Effects of Novel Priming and Boosting Strategies" *New Approaches to Vaccine Development*, Vienna, Apr. 1995.

Malone, R.W., et al. "Mucosal Immune Responses Associated with Polynucleotide Vaccination" *New Approaches to Bacterial Vaccine Development*, Munich, Germany, May 1996.

Malone, J.G., et al. "Mucosal Immune Responses Associated with Polynucleotide Vaccination" *Behring Inst. Mitt.* 98:1–10, 1996.

Ulmer, J.B., et al. "Prospects for Induction of Mucosal Immunity by DNA Vaccines" *Mucosal Vaccines* 8:119–127, Academic Press Inc., 1996.

Kuklin, N., et al. "Induction of Mucosal Immunity against Herpes Simplex Virus by Plasmid DNA Immunization" *J. Virol.* 71:3138–3145, 1997.

Dixon, B., "The Third Vaccine Revolution" cmt *Bio/Technology* 13:420, 1995.

Robbins–Roth, C., Ed. "Cancer Vaccines: Are We Finally on the Right Track?" *Bioventure View* Oct. 12, 1997.

Haynes et al. "Scientific and Social Issues of Human Immunodeficiency Virus Vaccine Development" Science vol. 260:1279–1286, May 28, 1993.

Verma et al. "GeneTherapy—Problems and Prospects" Nature vol. 389:239–242, Sep. 18, 1997.

*Primary Examiner*—John S. Brusca
*Assistant Examiner*—Sean McGarry
*Attorney, Agent, or Firm*—Shanks & Herbert

[57] ABSTRACT

The invention consists of a method for inducing production of a mucosal immune response in a host by administration of an antigen-encoding polynucleotide preparation, comprising DNA or RNA encoding an antigenic epitope to a mucosal inductor site in the mucosal tissue of the host. Naked DNA may be administered directly to mucosa, for instance in saline drops, or in a recombinant gene expression vector. Preferably, the recombinant gene expression vectors are not capable of replication or dessimination. The invention also includes the use of live viral vaccines wherein the viruses include immunostimulatory polynucleotides of the invention. According to a preferred method of the invention, a target protein antigen is administered through its expression by a recombinant gene expression vector.

38 Claims, 3 Drawing Sheets

DNA VACCINES FOR ELICITING A MUCOSAL IMMUNE RESPONSE

This application claims benefit of Provisional application Ser. No. 60/018,269 filed May 24, 1996.

STATEMENT OF FEDERALLY SPONSORED RESEARCH

Support for the research disclosed herein was provided by the U.S. Army under Grant No. DAMD17-94-J4436. The Government has certain rights in this invention.

FIELD OF THE INVENTION

The invention relates to methods and reagents for immunizing a host against an antigen. Specifically, the invention relates to polynucleotide vaccines for eliciting mucosal immune responses and methods for their use.

BACKGROUND OF THE INVENTION

A variety of gene delivery technologies can be used to express antigens within somatic tissues, resulting in systemic humoral and cellular immune responses. This observation has led to the development of polynucleotide vaccine preparations for stimulation of systemic immunity.

In the late 1980s, it became apparent that the direct injection of plasmid DNA or mRNA into a variety of tissues would result in polynucleotide uptake and expression of encoded proteins (U.S. Pat. No. 5,580,859). These data resulted in the development of a gene transfer-based vaccine paradigm. Realizing the importance of cytotoxic cellular immune responses, it was further proposed that genetic immunization could be used to stimulate both humoral and cellular immunity (U.S. Pat. No. 5,589,446). Subsequent experimentation demonstrated that direct gene transfer into tissues can elicit complete systemic immune responses to a variety of antigens (Ulmer et al., *Science* 259:1745–1749, 1993; Wang et al, *Proc Natl Acad Sci USA* 90(9):4156–4160, 1993). A number of studies have since extended the DNA vaccine model to include a wide variety of gene delivery systems and therapeutic applications.

More recently, research concerning potential therapeutic uses for naked gene expression vectors has focused on enhancing gene expression through use of different promotors, delivery vehicles and routes of administration (see, e.g., Stribling, et al., *Proc. Natl. Acad. Sci. USA*, 89:11277–11281, 1992 [expression following aerosol delivery of a gene occurred with use of a liposomal delivery system]; and, Tang, et al., *Nature*, 356:152–154, 1992 [injection with a vaccine "gun" of an hGH plasmid coupled to colloidal gold beads]).

The immune system can be divided into two functionally independent compartments: the systemic compartment, which is represented by the bone marrow, spleen, and lymph nodes, and the mucosal compartment, which is represented by lymphoid tissues in mucosae and external secretory glands. A consequence of this compartmentalization is that systemic routes of immunization are usually of limited value for the prevention of mucosa-contracted diseases. Studies performed in animal models and with humans have convincingly demonstrated that the level of protection against diseases of the respiratory, genital, or intestinal tract correlate better with the levels of antibodies in corresponding external secretions than in serum.

In general, current polynucleotide vaccine strategies focus on the stimulation of systemic humoral and/or cellular immune responses to specific antigens. Unfortunately, the majority of infectious disease is acquired via mucosal surfaces, and systemic polynucleotide vaccine strategies do not typically elicit mucosal immune responses. For instance, a common route for the initial acquisition of HIV involves passage of the virus across a mucosal surface. Disruption of the mucosa allows the virus to reach the underlying lymphoid cells in the lamina propria. Secretory immunoglobulins A (sIgA) may function as a first line of defense against such infections, preventing attachment and transmission through the mucosa. In addition, it is believed that sIgA can inhibit viral replication within infected epithelial cells.

Like the systemic immune compartment, the common mucosal immune system requires mechanisms for selective switching between the expansion of effector cells and the induction of tolerance. Inappropriate induction of mucosal immune responses can result in clinical syndromes including food and respiratory allergies (Holt and McMenamin, *Clin Exp Allergy* 19(3): 255–62, 1989; Brandtzaeg et al.(1993) The serologic and mucosal immunologic basis of celiac disease. *Immunophysiology of the Gut. Bristol-Meyers squibb/Mead Johnson Nutrition Symposia* Eds. W. A. Walker, P. R. Harmatz and B. K. Wershil. London., Academic press. 295–333). The mechanism(s) involved in switching between induction or suppression of mucosal immune responses remain to be resolved, but may involve antigen sampling and presentation by either specialized inductor tissues (stimulation) or MHC Class II$^+$ mucosal epithelial cells (tolerance in gut (Brandtzaeg et al., *Gastroenterology* 97(6): 1562–84, 1989), hypersensitivity or tolerance in lung (Kalb et al., *Am J Respir Cell Mol Biol* 4(4): 320–9. 1991)). These studies illustrate the complex nature of mucosal immune response regulation, and support the hypothesis that selection of different tissues for transfection or transduction with a mucosal polynucleotide vaccine may result in profound differences in the resulting pattern of immune response.

Mucosal immunity typically involves both cellular cytotoxic as well as antibody-mediated responses. Production of secreted IgA is a widely accepted surrogate marker for complete mucosal immune responses. Efforts to raise sIgA using current polynucleotide vaccination methods have been inconclusive. The pathways by which mucosal immune response can be elicited have not been fully characterized. Mucosal antigen presentation can be associated with either immunologic stimulation or induction of tolerance. Hence, there are multiple hypotheses for the absence of IgA in lung lavage and nasal secretion samples collected after mucosal expression of an antigenic protein via DNA vaccination. Alternative hypotheses include inadequate gene transfer and expression and inappropriately targeted gene transfer and expression.

Discrimination between these hypotheses requires an efficient gene delivery and expression vector system which is replication-defective. Such system is required for testing the importance of anatomic targeting for enabling mucosal immune responses. Therefore, one system meeting these criteria involves an engineered Semliki Forest Virus (SFV) alphaviruses (Liljestrom and Garoff, *Biotechnology* (*N Y*) 9(12): 1356–61. 1991). Alphaviruses are positive strand RNA viruses, and hence the RNA genomes of these agents produce infectious particles upon transfection (Zhou et al., *Vaccine* 12(16): 1510–4. 1994) The Semliki Forest virus (SFV) has been engineered to yield a vector system based on a genomic SFV cDNA inserted into an SP6 RNA promoter plasmid. The resulting plasmid has been modified by deletion of the SFV structural genes to allow insertion of a heterologous cDNA as part of the SFV replicon. After incorporation of the cDNA of interest, in vitro SP6 transcription of plasmid DNA results in mRNA preparations which encode both the recombinant protein as well as the SFV replicase, which can be assembled into viral particles and used to infect cells. Typically after infection, the polymerase and recombinant protein become a major fraction of total cellular protein (Liljestrom and Garoff 1991). Subsequent cytotoxicity typically limits expression of the recombinant protein to four to seven days.

One potential complication of all virally-derived gene transfer systems is the development of replication-competent helper virus. In alphavirus-derived systems, this occurs via polymerase strand crossover between the mRNA which encodes the protein of interest, and a trans helper mRNA which provides packaging proteins used to produce defective particles for transduction. By modifying the viral spike protein encoded by SFV, conditionally infectious particles which require activation by chymotrypsin can be produced, and this modification has reduced the production of replication-competent helper particles to undetectable levels (Berglund et al., *Biotechnology* (*N Y*) 11(8): 916–20. 1993). Therefore, gene delivery and expression remain confined to the site of initial innoculation. Recombinant SFV mRNA and defective particles have been shown to stimulate a strong systemic immune response to a recombinant protein after genetic vaccination (Zhou et al. 1994; Zhou, Berglund et al. 1995)

Thus, the need exists for a safe and effective means of introducing nucleotides that will express in vivo a peptide or protein which can induce mucosal immunity to vaccinate a host against, for example, respiratory illnesses, sexually transmitted diseases, and other diseases which are initially contracted through the mucosa.

In the instant invention, we have exploited this efficient transduction and expression activity of recombinant SFV particles to test the hypothesis that mucosal genetic vaccines will require gene transfer methods which target specific mucosal-associated inductor tissues such as the oropharyngeal Waldeyer's ring or intestinal Peyer's patches.

SUMMARY OF THE INVENTION

In one aspect, the invention comprises a method for transfection of polynucleotides which express immunogenic proteins into cells of mucosal tissue located at mucosal inductor sites so as to result in a mucosal immune response to the encoded antigens wherein secretory IgA antibodies are produced to the encoded antigens. In another aspect, the invention comprises a method for inducing a protective mucosal response against mucosal-contracted pathogens, such as respiratory, intestinal and vaginal viruses by administration to a vertebrate of a polynucleotide vaccine.

An antigen-encoding polynucleotide preparation, comprising recombinant expression vectors, such as chimeric viral vectors, for use in genetic immunization via mucosal administration are also provided herein. The antigen-encoding polynucleotide preparation of the invention can include immunostimulatory polynucleotides which help to elicit a vigorous mucosal humoral immune response.

As used with respect to the invention, the term "antigen-encoding polynucleotide preparation" refers to plasmids or cosmids which encode a peptide or protein of interest (e.g., antigens, cytokines, chemokines, heat-shock proteins, and other immunomodulatory agents). The vector may contain a gene encoding an adjuvant, such as the cholera toxin B subunit, to enhance the immunostimulatory effect of the vaccine. In addition to cholera toxin, other natural compounds with mucosal adjuvant properties are streptococcal antigen, and the heat labile toxin (LT) of *E. coli.*

The present invention exploits the discovery that gene expression delivery systems directed to mucosal inductor sites adjacent to or containing "mucosal-associated lymphoid aggregates" (MALT) in the mucosal tissue can elicit antigen expression therein with resulting mucosal immune responses, including secretion of sIgA. Such mucosal inductor sites are found in the tonsils and nasal lymphoid tissue, (the Waldeyer's ring of oropharyngeal lymphoid tissue in the nasal, palatinal and lingual tonsils)), in bronchus-associated lymphoid tissue (BALT), and in gut-associated lymphoid tissue (Peyer's patches). The effector sites from which sIgA is secreted may be located in anatomically remote glands, such as the lacrimal, salivary and mammary glands, as well as in the nasal mucosa, upper respiratory tract, small intestine, large intestine and genital tract. A unique cooperation between the mucosal B-cell system and the secretory component (SC) expressed basolaterally on glandular epithelial cells accounts for this phenomenon. The B cells responsible for local sIg production are initially stimulated in MALT cells, from which they migrate as memory cells to exocrine tissues all over the body. Mucous membranes are thus furnished with secretory antibodies in an integrated way, ensuring a variety of specificities at every secretory site.

The present invention exploits this integrated system by administering polynucleotide vaccines so as to contact cells located at mucosal inductor sites, especially those in the gut, genital, and upper and lower respiratory system, and thereby advantageously promote production of sIgA to titer levels that are protective against diseases caused by pathogens, especially respiratory, genital, and enteric viruses, which initially enter the body through the mucosa.

The antigen-encoding polynucleotide preparation may also encode polypeptides of interest, such as additional antigens or adjuvants and cytokines. The preferred vectors for use in the method of this invention are viral recombinant gene expression vectors and non-viral recombinant gene expression vectors associated with delivery vehicles (e.g., liposomes or colloidal particles) into which polynucleotides of the invention have been inserted. In addition, using the same techniques by which polynucleotides of the invention are incorporated into viral gene expression vectors, the polynucleotides may be incorporated into live viral vaccines to augment the immune response to viral antigens.

For purposes of monitoring gene expression or testing immune response, these vectors may be modified to include known reporter or antigen genes. For example, the pRSV lac-Z DNA vector described in Norton, et al., *Mol. Cell. Biol.,* 5:281, (1985), may produce β-galactosidase with protein expression. β-Galactosidase has also been used as a test antigen expressed from recombinant SFV vectors. Luciferase and chloramphenicol acetyl transferase ("CAT"; see, e.g., Gorman, et al., supra, re construction of a pRSV-CAT plasmid) may also be used. Convenient plasmid propagation may be obtained in *E. coli* (see, e.g., *Molecular Cloning: A Laboratory Manual,* supra.)

For use as a tolerizing vaccine, a mixture of polynucleotides or separately coadministered group of polynucleotides may include a gene operatively encoding for an immunosuppressive cytokine (such as TGFβ) and a separate gene operatively encoding for a relevant histocompatibility protein. This approach could be adapted for use in inducing tolerance to foreign antigens (including alloantigens) as well as self-antigens.

In the preferred embodiment, the invention comprises a method for immunizing a host against antigen using gene expression vectors of the invention. According to a preferred method of the invention, such expression vectors are introduced into mucosal tissues of the host having a relatively high concentration of mucosal inductor tissue therein. Introduction of the antigen-encoding polynucleotide preparation into the host may be by any suitable means known in the art.

BRIEF DESCRIPTION OF THE DRAWINGS

Figures 1A, 1B:
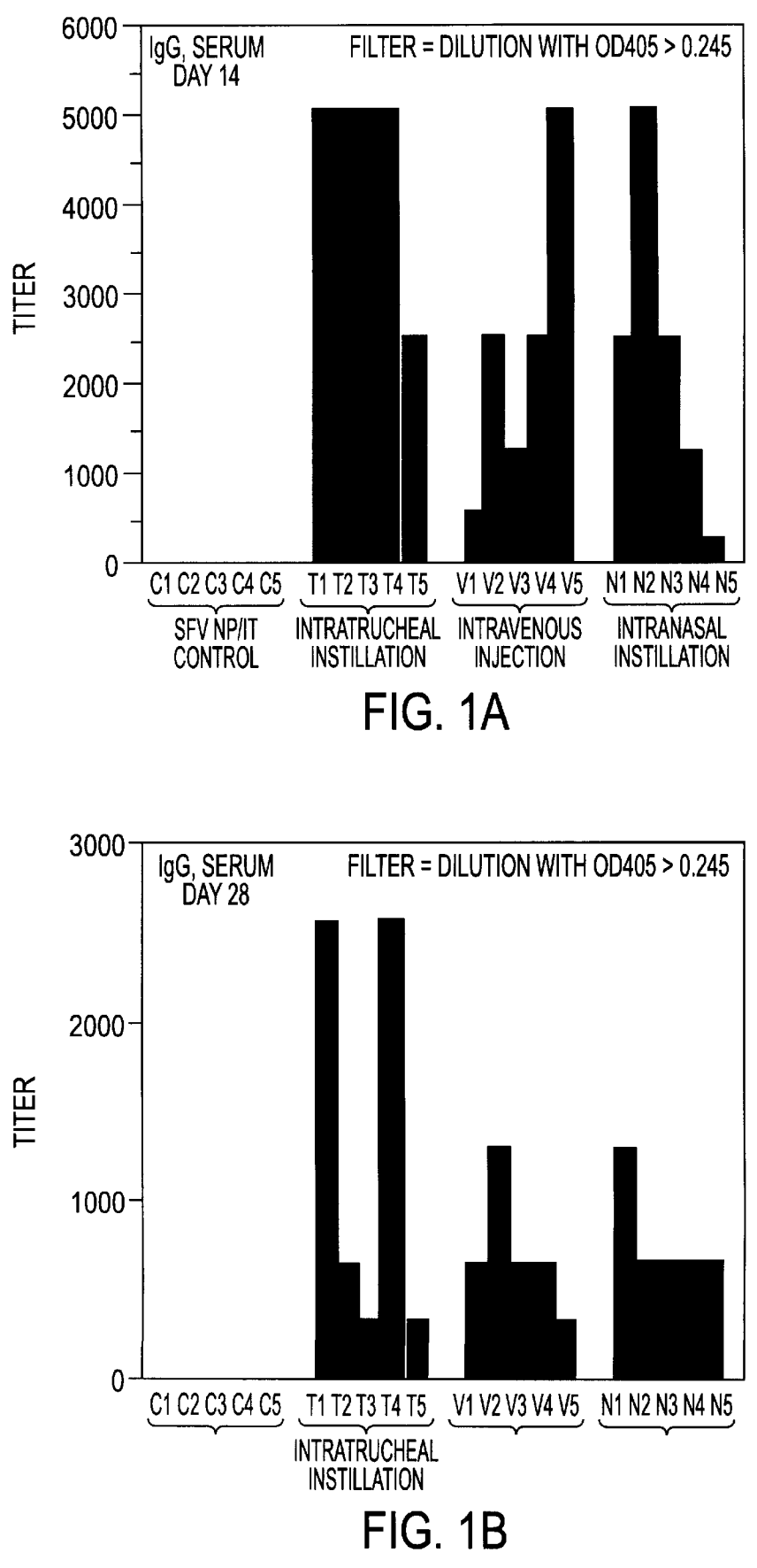

FIGS. 1A and 1B is the ELISA analysis of serum titers of the IgG obtained at 14 (FIG. 1A) and 28 (FIG. 1B) days from mice immunized with recombinant SFV particles. Groups of five female SPF Balb-C mice were immunized with either a control expression vector (Helper 2/SFV-NP) via intratracheal administration (C1–C5), or via intratracheal (T1–T5), intravenous (V1–V5) or intranasal (N1–N5) administration of SFV particles which confer expression of the test antigen β-galatosidase (Helper2/SFV-LacZ). Titer was defined as the most dilute serum sample which reacted to produce a $OD_{405}$ of 2.5 times above the average signal obtained with control serum.

DETAILED DESCRIPTION OF THE INVENTION

Figure 2A:
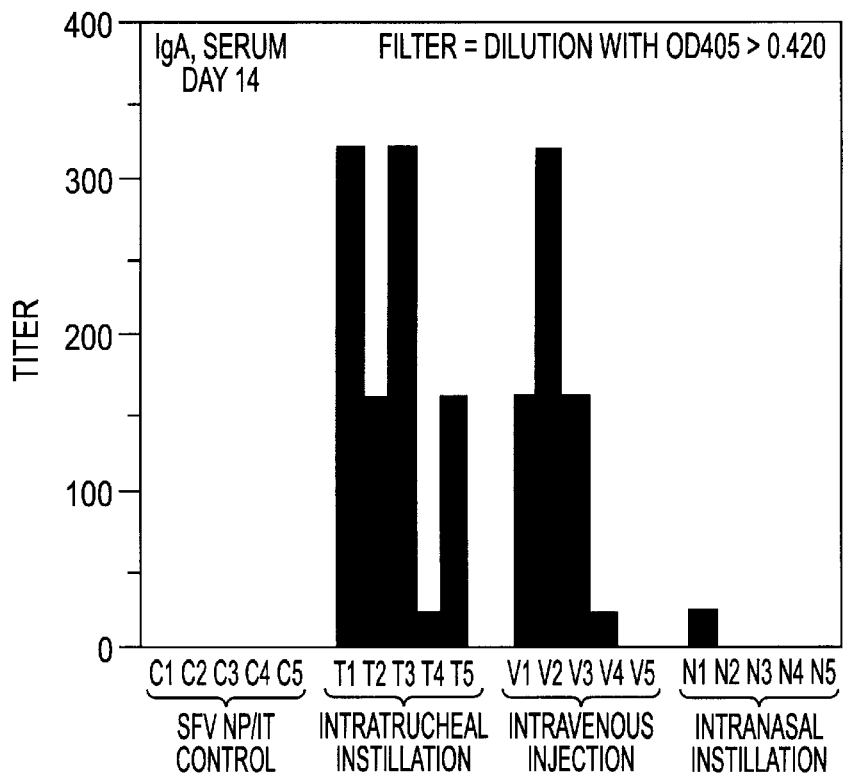
FIGS. 2A and 2B: ELISA analysis of serum titers of IgA obtained at 14 (FIG. 2A) and 28 (FIG. 2B) days from mice immunized with recombinant SFV particles. Groups of five female SPF Balb-C mice were immunized with either a control expression vector (Helper 2/SFV-NP) via intratracheal administration (C1–C5), or via intratracheal (T1–T5), intravenous (V1–V5) or intranasal (N1–N5) administration of SFV particles which confer expression of the test antigen β-galatosidase (Helper2/SFV-LacZ). Titer was defined as the most dilute serum sample which reacted to produce a $OD_{405}$ of 2.5 times above the average signal obtained with control serum.
Figure 2B:
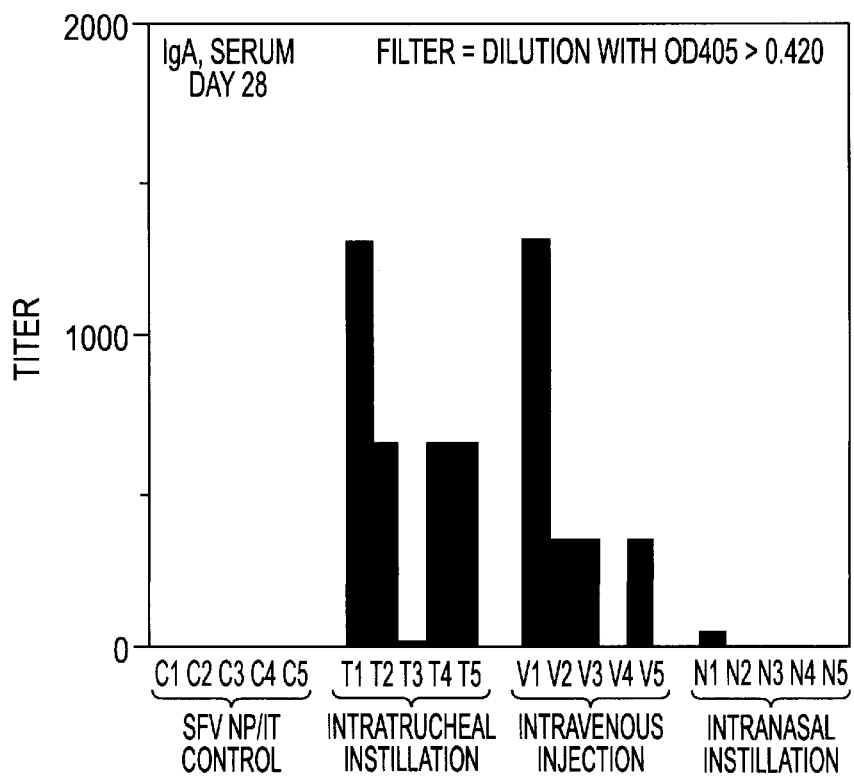

I. Immunostimulatory Polynucleotides for Use in the Gene Expression Vectors of the Invention The polynucleotides of the invention are antigen-encoding polynucleotide preparations, such as DNA, which can be inserted into a gene expression vector, such as a viral vector or plasmid DNA, by techniques well known to those of ordinary skill in the art (see, e.g., Section II, infra). Suitable polynucleotide sequences for use as restriction sites, linkers and the like may be included in the polynucleotide of the invention to be inserted into the gene expression vector.

Those of ordinary skill in the art will readily be able to identify polynucleotides which stimulate production of sIgA in vivo when administered to mucosal inductor sites, including those adjacent to or containing local aggregates of "mucosal associated lymphoid tissue" (MALT), as measured by conventional detection techniques (such as those described in the Examples, infra).

A. Preparation of polynucleotides for insertion into the gene expression vectors used in the practice of the invention.

As used herein, "polynucleotide preparation" refers to a polymer of deoxyribonucleotides or ribonucleotides, in the form of a separate fragment or as a component of a larger construct. The immunostimulatory polynucleotides of the invention may be double or single-stranded DNA or RNA either administered to mucosal tissue in a saline solution or inserted into recombinant expression vectors, preferably viral or bacterial plasmid gene expression vectors. Such polynucleotides must also be either non-replicating or engineered by means well known in the art so as not to replicate into the host genome. The recombinant gene expression vectors of the invention may also include coding regions for expression of antigens, cytokines, heat shock proteins, chemokines, T cell epitopes immunostimulatory sequences and other immunotherapeutically significant polypeptides.

Screening procedures which rely on nucleic acid hybridization make it possible to isolate any polynucleotide sequence from any organism, provided the appropriate probe or antibody is available. Oligonucleotide probes, which correspond to a part of the sequence encoding the protein in question, can be synthesized chemically. This requires that short, oligo- peptide stretches of amino acid sequence must be known. The DNA sequence encoding the protein can also be deduced from the genetic code, however, the degeneracy of the code and codon usage for the species of interest must be taken into account.

For example, a cDNA library believed to contain a polynucleotide of interest can be screened by injecting various mRNA derived from cDNAs into oocytes, allowing sufficient time for expression of the cDNA gene products to occur, and testing for the presence of the desired cDNA expression product, for example, by using antibody specific for a peptide encoded by the polynucleotide of interest or by using probes for the repeat motifs and a tissue expression pattern characteristic of a peptide encoded by the polynucleotide of interest. Alternatively, a cDNA library can be screened indirectly for expression of peptides of interest having at least one epitope using antibodies specific for the peptides. Such antibodies can be either polyclonally or monoclonally derived and used to detect expression product indicative of the presence of cDNA of interest. In another embodiment, the DNA library can be generated from mRNA obtained from a biological sample using either standard reverse transcriptase synthesis or polymerase chain reaction (PCR) amplification of reverse transcribed mRNA or direct PCR amplification of DNA, the composition of the resulting polynucleotides can be compared to known samples using techniques (including sequence analysis and differential display) known to those skilled in the art, and selected DNA fragments can be used for recombination to provide appropriate expression vectors.

Polynucleotides for use in the invention can also be synthesized using techniques and nucleic acid synthesis equipment which are well-known in the art. For reference in this regard, see Ausubel, et al., *Current Protocols in Molecular Biology*, Chs. 2 and 4 (Wiley Interscience, 1989) (genomic DNA); and, Maniatis, et al., *Molecular Cloning: A Laboratory Manual* (Cold Spring Harbor Lab., New York, 1982) (cDNA). For ease of construction and use, synthesized polynucleotides and cDNAs are generally preferred for use in the recombinant gene expression vectors of the invention.

The recombinant gene expression vectors used in the practice of the invention may be constructed to include coding regions for peptides of diagnostic (i.e., marker proteins), therapeutic or immunostimulatory interest. For example, a mixture of polynucleotides or separately coadministered group of polynucleotides may be of use in immunizing a host against more than one antigen and/or to further stimulate a host immune response (by, for example, including a gene operatively encoding for an immunosuppressive cytokine such as TGFβ or a relevant histocompatibility protein in the recombinant gene expression vector).

The recombinant gene expression vectors of the invention may also encode peptides having more than one biological activity. For example, a polynucleotide operatively encoding for a peptide may be coupled to or administered with a polynucleotide operatively encoding an antibody in such a way that both peptide and antibody will be expressed. Further, the same vector may also encode an antigen, T cell epitope, cytokine or other polypeptides or immunostimulatory sequences in combination.

The term "antibody" encompasses whole immunoglobulin of any class, chimeric antibodies, hybrid antibodies with dual or multiple antigen specificities and fragments including hybrid fragments. Also included within the meaning of "antibody" are conjugates of such fragments, and so-called antigen binding proteins (single chain antibodies) as described, for example, in U.S. Pat. No. 4,704,692. Alternatively, the encoded antibodies can be anti-idiotypic antibodies (antibodies that bind other antibodies) as described, for example, in U.S. Pat. No. 4,699,880.

Up to 200 polynucleotide sequences under the control of a single promoter can be expressed by an appropriate plasmid or cosmid. Such "cocktail" vectors will be of particular use in eliciting a protective mucosal immune response against or in treating infections by agents of different species which cause similar symptoms. For example, there are over 100 known species of rhinoviruses which cause respiratory illnesses having similar clinical symptoms. Rather than undertaking the identification of the particular infecting species (a laborious and often inexact process), a cocktail vaccine could be administered according to the method of the invention which is capable of stimulating an immune response to many different rhinoviruses. This approach also allows for the construction of a vaccine to various strains of HIV, using pooled isolates of envelope genes from different patients (which genes may, if necessary, then be amplified).

Known polynucleotide sequences for genes encoding such polypeptides of interest will be readily accessible to, or known by, those of ordinary skill in the art. Those of skill in the art will appreciate that the methods of the invention may be adapted for use in administering any polynucleotide or mixture thereof which operatively encode therapeutic and/or immunogenic peptides of interest. The invention is therefore not limited to use with any particular polynucleotide(s).

II. Methods for Construction of Recombinant Gene Expression Vectors

The antigen-encoding polynucleotide preparations of the invention are preferably recombinant gene expression vectors, which are preferably plasmids or cosmids, but may also be recombinant viruses, alphaviruses, adenoviruses, adeno-associated viruses or retroviruses. As discussed above, the vectors may also include gene(s) which operatively encode a peptide/antigen of interest (e.g., cytokines). For convenience, the term "plasmid" as used in this disclosure will refer to plasmids, cosmids, or other DNA fragments depending on which is appropriate to use for expression of the peptide of interest (where the choice between the two is dictated by the size of the gene encoding the peptide of interest). "Operatively encode" refers to a gene which is associated with all of the regulatory sequences required for expression of a polypeptide.

Polynucleotides of the invention may be conjugated to or used in association with other polynucleotides that operatively code for regulatory proteins that control the expression of these polypeptides or may contain recognition, promoter and secretion sequences. Those of ordinary skill in the art will be able to select regulatory polynucleotides and incorporate them into the recombinant gene expression vectors of the invention (if not already present therein) without undue experimentation. For example, suitable promoters for use in murine or human systems and their use are described in Ausubel, *Current Protocols in Molecular Biology, supra* at Ch. 1.

In general, plasmid vectors which may be used in the invention contain promoters and control sequences which are derived from species compatible with the host cell. For example, *E. coli* is typically transformed using pBR322, a plasmid derived from an *E. coli* species (Bolivar, et al., *Gene*, 2:95, 1977). pBR322 contains genes for ampicillin (AMPR) and tetracycline resistance (the former of which includes polynucleotide fragments useful in the invention) and thus provides easy means for identifying transformed cells. However, for use in humans, the U.S. Food and Drug Administration presently prohibits use of recombinant expression vectors which may confer ampicillin resistance to the host. The pBR322 plasmid, or other microbial plasmid must also contain or be modified to contain promoters and other control elements commonly used in recombinant DNA construction.

"Control sequence(s)" or "control region" refers to specific sequences at the 5' and 3' ends of eukaryotic genes which may be involved in the control of either transcription or translation. Virtually all eukaryotic genes have an AT-rich region located approximately 25 to 30 bases upstream from the site where transcription is initiated. Another sequence found 70 to 80 bases upstream from the start of transcription of many genes is a CCAAT region where X may be any nucleotide. At the 3'end of most eukaryotic genes is an AATAAA sequence which may be the signal for additional of the poly A tail to the 3'end of the transcribed mRNA. Efficiently expressed genes also frequently encode mRNA sequences which are removed during RNA processing, known as introns, which also provide control functions and can aid in the expression of a peptide or protein-encoding recombinant polynucleotide.

For those vectors for use in recombinant gene delivery systems of the invention that include genes which operatively encode polypeptides or immunomodulatory sequences of interest, preferred promoters controlling transcription from vectors in mammalian host cells may be obtained from various sources, for example, the genomes of viruses such as polyoma, Simian Virus 40 (SV40), adenovirus, retroviruses, hepatitis-B virus and most herpesviruses preferably cytomegalovirus, or from heterologous mammalian promoters, e.g. beta actin promoter. The early and later promoters of the SV40 virus are conveniently obtained as an SV40 restriction fragment which also contains the SV40 viral origin of replication (Fiers, et al, *Nature*, 273:113, 1978). The immediate early promoter of the human cytomegalovirus is conveniently obtained as a HindIII E restriction fragment (Greenaway, et al., *Gene*, 18:355–360, 1982). Promoters from the host cell or related species also are useful herein.

Promoters suitable for use with prokaryotic hosts illustratively include the β-lactamase and lactose promoter systems (Chang, et al., *Nature*, 275:615, 1978; and Goeddel, et al., *Nature*, 281:544, 1979), alkaline phosphatase, the tryptophan (trp) promoter system (Goeddel, *Nucleic Acids Res.*, 8:4057, 1980) and hybrid promoters such as the taq promoter (de Boer, et al., *Proc. Natl. Acad. Sci. USA*, 80:21–25, 1983). However, other functional bacterial promoters are suitable. Their nucleotide sequences are generally known in the art, thereby enabling a skilled worker to ligate them to a polynucleotide which encodes the peptide of interest (Siebenlist, et al., *Cell*, 20:269, 1980) using linkers or adapters to supply any required restriction sites.

In addition to prokaryotes, eukaryotic microbes such as yeast cultures may also be used as source for control sequences. *Saccharomyces cerevisiae*, or common baker's yeast is the most commonly used eukaryotic microorganism in this context, although a number of other strains are commonly available.

Suitable promoting sequences for use with yeast hosts include the promoters for 3-phosphoglycerate kinase (Hitzeman, et al., *J. Biol. Chem.*, 255:2073, 1980) or other glycolytic enzymes (Hess, et al. *J. Adv. Enzyme Reg.* 7:149, 1968; and Holland, *Biochemistry*, 17:4900, 1978) such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degraded enzymes associated with nitrogen metabolism, metallothionine, glyceraldehyde-3-phosphate dehydrogenase, and enzymes responsible for maltose and galactose utilization. Yeast enhancers also are advantageously used with yeast promoters.

Transcription of DNA encoding a polypeptide of interest by higher eukaryotes is increased by inserting an enhancer sequence into the vector. Enhancers are cis-acting elements of DNA, usually about from 10–300 bp, that act on a promoter to increase its transcription. Enhancers are relatively orientation and position independent having been found 5' (Laimins, et al., *Proc.Natl.Sci.Acad.USA*, 78:993, 1981) and 3' (Lusky, et al., *Mol. Cell Bio.*, 3:1108, 1983) to the transcription unit, and within an intron (Banerji, et al., *Cell*, 33:729, 1983) as well as within the coding sequence itself (Osborne, et al., *Mol. Cell Bio.*, 4:1293 1984). Many enhancer sequences are now known from mammalian genes (globin, elastase, albumin, a-feto-protein and insulin). Typically, however, an enhancer from a eukaryotic cell virus will be used. Examples include the SV40 enhancer on the late side of the replication origin (bp 100–270), the cytomegalovirus early promoter enhancer, the polyoma enhancer on the late side of the replication origin, and adenovirus enhancers.

Expression vectors that contain a gene which operatively encodes a polypeptide antigen and are intended to be introduced into eukaryotic host cells, such as epithelial cells lining mucosa, and also including dendritic cells associated with mucosa or derived from tissue, will also contain sequences necessary for the termination of transcription which may affect mRNA expression. Expression vectors may also contain a selection gene, also termed a selectable marker. Examples of suitable selectable markers for mammalian cells which are known in the art include dihydrofolate reductase (DHFR), thymidine kinase or neomycin. When such selectable markers are successfully transferred into a mammalian host cell, the transformed mammalian host cell can survive if placed under selective pressure (i.e., by being conferred with drug resistance or genes altering the nutrient requirements of the host cell).

Those of ordinary skill in the art will be familiar with, or may readily ascertain the identity of, viruses and retroviruses for use as recombinant expression vectors. Skilled artisans will also be familiar with and able to construct invasive bacteria which may be modified for use as recombinant delivery and expression vectors. Preferred examples of bacterial delivery systems include salmonella and shigella based vectors. Such artisans will also be able to construct non-viral vectors associated with delivery vehicles such as liposomes or colloidal particles without undue experimentation. Therefore, only a brief summary regarding such viral and non-viral vectors will be provided here for review.

A colloidal dispersion system may be used for targeted delivery of DNA. Colloidal dispersion systems include macromolecule complexes, nanocapsules, microspheres, beads, and lipid-based systems including oil-in-water emulsions, micelles, mixed micelles, and liposomes. The preferred colloidal system of this invention is a lipid preparation including unilamaller and multilamellar liposomes.

Liposomes are artificial membrane vesicles which are useful as delivery vehicles in vitro and in vivo. It has been shown that large unilamellar vesicles (LUV), which range in size from 0.2–4.0 μm can encapsulate a substantial percentage of an aqueous buffer containing large macromolecules. RNA, DNA and intact virions can be encapsulated within the aqueous interior and be delivered to cells in a biologically active form (Fraley, et al., *Trends Biochem. Sci.*, 6:77, 1981). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes encoding the polynucleotides at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., *Biotechniques*, 6:682, 1988). In addition to such LUV structures, multilamellar and small unilaellar lipid preparations which incorporate various cationic lipid amphiphiles can also be mixed with anionic polynucleotides to form nucleolipidic particles which are often also refered to as liposomes (Felgner, et al, Proc Natl Acad Sci U S A 84 (21): 7413 1987) and used to deliver the nucleic acids into cells.

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations. The appropriate composition and preparation of cationic lipid amphiphile:polynucleotide formulations are known to those skilled in the art, and a number of references which provide this information are available (Bennett, et al, J. Of Liposome Research 6(3):545).

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14–18 carbon atoms, particularly from 16–18 carbon atoms, and is saturated. Illustrative phospholipids include egg phosphatidylcholine, dipalmitoylphosphatidylcholine and distearoylphosphatidylcholine. Examples of cationic amphiphilic lipids useful in formulation of nucleolipid particles for polynucleotide delivery include the monovalent lipids DOTAP, DOTMA, and DC-Chol, the polyvalent lipids LipofectAMINE, DOGS, Transfectam and other amphiphilic polyamines. These agents may be prepared with helper lipids such as Dioleoyl Phosphatidyl Ethanolamine or with adjuvants including cholera derived molecules including cholera toxin.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand.

Various viral vectors that can be utilized in the practice of the invention include adenovirus, adeno-associated virus, herpes virus, vaccinia, or, preferably, an RNA virus such as a retrovirus or an alphavirus. Preferably, the retroviral vector is a derivative of a murine or avian retrovirus. Preferably the alphavirus vector is derived from Sindbis or Semliki Forest Virus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes. All of these vectors can transfer or incorporate a gene for a selectable marker so that transduced cells can be identified and generated.

By inserting one or more sequences of interest into the viral vector, along with another gene which encodes the ligand for a receptor on a specific target cell, for example, the vector is now target specific. Retroviral vectors can be made target specific by inserting, for example, a polynucleotide encoding a sugar, a glycolipid, or a protein. Preferred targeting is accomplished by using an antibody to target the retroviral vector, such as to the vicinity of a mucosal inductor site, using a MALT-specific antibody. Those of skill in the art will know of, or can readily ascertain without undue experimentation, specific polynucleotide sequences which can be inserted into the retroviral genome to allow target specific delivery of the retroviral vector containing the polynucleotides of interest.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence that enables the packaging mechanism to recognize an RNA transcript for encapsidation. Helper cell lines that have deletions of the packaging signal include, but are not limited to, Y2, PA317 and PA12, for example. These cell lines produce empty virions, since no genome is packaged. If a retroviral vector is introduced into such helper cells in which the packaging signal is intact, but the structural genes are replaced by other genes of interest, the vector can be packaged and vector virion can be produced.

It will be appreciated that the same techniques which are utilized to incorporate the immunostimulatory polynucleotides of the invention into viral gene expression vectors may be used to incorporate the sequences into live and attenuated live viruses for use as vaccines. Such modified viral vaccines can be expected to have greater immunostimulatory properties than would be found in the viral vaccine itself.

Targeting can also be confered by physical means. For example, since the mucosal inductive tissue of the nasopharynx, also known as Waldeyer's ring, is located in the posterior nasopharynx of man, physical manipulations can be performed which direct the application, adhesion and transfection of viral or non-viral polynucleotide delivery vehicles to the posterior oropharynx, thereby directing the vehicles to deliver the polynucleotide and express the appropriate immunogenic or immunomodulatory properties encoded or provided by the vector. Such means are readily apparent, and include the use of oral washes, oral sprays, nasal drops, and application of various aerosols including dry aerosols.

Targeting of mucosal tissues can be performed by exploiting inherent biological properties of the lymphoid bed which is to be targeted. These include the crypt architecture of the tonsillar pillars which can be used to entrap particles, and also include the M cells of Peyer's patches in the gut, which M cells specifically endocytose a wide variety of particles including lipidic particles and other small particulates. Therefore, those skilled in the art can prepare a wide variety of molecular particulate preparations which, if provided to intestine, will lodge within the crypt portions of intestinal peyers patches and be endocytosed by M cells. If such particles provide for delivery of a biologically active polynucleotide to M cells, then such particles will enable the stimulation or modulation of mucosal immune response induction by the Peyer's patch lymphoid tissue to which the M cell traffics.

Construction of suitable vectors containing desired coding, non-coding and control sequences employ standard ligation techniques. Isolated plasmids or DNA fragments are cleaved, tailored, and re-ligated in the form desired to construct the plasmids required.

For example, for analysis to confirm correct sequences in plasmids constructed, the ligation mixtures may be used to transform a host cell and successful transformants selected by antibiotic resistance where appropriate. Plasmids from the transformants are prepared, analyzed by restriction and/or sequenced by, for example, the method of Messing, et al., (*Nucleic Acids Res.*, 9:309, 1981), the method of Maxam, et al., (*Methods in Enzymology*, 65:499, 1980), or other suitable methods which will be known to those skilled in the art. Size separation of cleaved fragments is performed using conventional gel electrophoresis as described, for example, by Maniatis, et al., (*Molecular Cloning*, pp. 133–134, 1982).

Host cells may be transformed with the expression vectors of this invention and cultured in conventional nutrient media modified as is appropriate for inducing promoters, selecting transformants or amplifying genes. The culture conditions, such as temperature, pH and the like, are those previously used with the host cell selected for expression, and will be apparent to the ordinarily skilled artisan.

The most preferred vector for use in the method of this invention is a recombinant alphavirus vector system which expresses the lac Z gene (β-galactosidase). Construction of this vector is described in P. Liljestrom, *Current Opin. Biotechnol* 5(5):495–500, 1994; and P. Liljestrom et al., *Biotechnology (NY)* 9(12):1356–61, 1991, which is incorporated herein in its entirety by this reference.

Also, particularly useful vector constructs for use according to the invention are those which contain a promoter that can be switched "on" or "off" after the vector has been administered to a patient such as the ligand-inducible nuclear receptor promoters. Recombinant gene expression vectors containing such promoters are of particular use in vaccination protocols wherein the vector is introduced into the skin or mucosa, where expression can be controlled by applying the inducing ligand for absorption into the site at which the vector has been introduced.

Nuclear receptors represent a family of transcriptional enhancer factors that act by binding to specific DNA sequences found in target promoters known as response elements. Specific members of the nuclear receptor family include the primary intracellular targets for small lipid-soluble ligands, such as vitamin $D_3$ and retinoids, as well as steroid and thyroid hormones ("activating ligands").

Nuclear receptors activated by specific activating ligands are well suited for use as promoters in eukaryotic expression vectors since expression of genes can be regulated simply by controlling the concentration of ligand available to the receptor. For example, glucocorticoid-inducible promoters such as that of the long terminal repeat of the mouse mammary tumor virus (MMTV) have been widely used in this regard because the glucocorticoid response elements are expressed in a wide variety of cell types. One expression system which exploits glucocorticoid response elements responsive to a wide variety of steroid hormones (e.g., dexamethasone and progesterone) is a pGREtk plasmid (containing one or more rat tyrosine amino transferase glucocorticoid response elements upstream of the herpes simplex virus thymidine kinase (tk) promoter in pBLCAT8+), transfected in HeLa cells (see, Mader and White, *Proc.Natl.Acad.Sci USA*, 90:5603–5607, 1993 [pGRE2tk]; and, Klein-Hitpass, et al., *Cell*, 46:1053–1061, 1986 [pBLCAT8+]; the disclosures of which are incorporated herein by this reference to illustrate knowledge in the art concerning construction of suitable promoters derived from nuclear receptor response elements ["NRRE promoters"]). The pGREtk promoter is particularly effective in stimulating controlled overexpression of cloned genes in eukaryotic cells (Mader and White, supra at 5607).

Another particularly suitable NRRE promoter for use in the invention is one which is inducible by the vitamin $D_3$ compound 1,25-dihydroxyvitamin $D_3$ and non- hypercalcemic analogs thereof (collectively, "vitamin $D_3$ activating ligands"). NRRE promoters inducible by vitamin $D_3$ activating ligands contain the vitamin $D_3$ receptor (VDR) response elements PurG(G/T)TCA which recognizes direct repeats separated by 3 base pairs. Vitamin $D_3$ response elements are found upstream of human osteocalcin and mouse osteopontin genes; transcription of these genes is activated on binding of the VDR (see, e.g., Morrison and Eisman, *J.Bone Miner.Res.*, 6:893–899, 1991; and, Ferrara, et al., *J.Biol.Chem.*, 269:2971–2981, 1994, the disclosures of which are incorporated herein by this reference to illustrate knowledge in the art of vitamin $D_3$ responsive inducible promoters).).

Ferrara, et al. also described vitamin $D_3$ inducible promoters in recombinant expression vectors constructed using multiple copies of a strong VDR; in particular, the mouse osteopontin VDR (composed of a direct repeat of PurGT-TCA motifs separated by 3 base pairs). This VDR conforms to the PurGG/TTCA consensus motifs which have previously been shown to be responsive not only to vitamin $D_3$, but also to thyroid hormone and/or retinoic acid. As many as three copies of the mouse VDR was inserted into pBLCAT8+; immediately upstream of the herpes simplex virus tk promoter. Transfection of the resulting VDREtk vector into COS cells (producing a "VDR expression system") proved to be particularly useful in that COS cells contain the nuclear retinoid X receptor (RXR) that has been shown to act as an auxiliary factor for binding of VDR to its response element.

The VDR expression system (and functionally equivalent expression systems under the control of, for example, human osteocalcin gene promoter) is uniquely suited for use in the invention. Specifically, expression of a polynucleotide administered to a mammal according to the invention by mucosal routes (particularly the former) in a vitamin $D_3$ responsive expression system can be switched on by topical administration (i.e. by aerosol) of a 1,25-dihydroxyvitamin $D_3$ preparation at the point of entry (and off by withdrawing the vitamin $D_3$ preparation and/or modulated by applying or withdrawing a source of retinoic acid to or from the point of entry).

In vivo tests of the NRRE promoters indicate that they are inducible on systemic exposure to their corresponding response elements. Given the expected retention of polynucleotides administered intranasally at the point of entry (thus making them available for exposure to topically absorbed response elements), it can be reasonably predicted that use of NRRE promoters for expression of such polynucleotides will also permit their in vivo control through intranasal administration of appropriate NRRE promoter activating ligands (e.g., 1,25-dihydroxyvitamin $D_3$ transcriptional activators with a VDR expression vector for expression of the polynucleotide of interest).

Thus, use of an NRRE promoter recombinant gene expression vector for administration and expression of antigen-encoding immunostimulatory polynucleotides according to the invention permits control of expression to, for example, switch on expression when dosing is needed or switch off expression in the event of an adverse reaction to the expressed protein or peptide.

III. Pharmaceutical Preparations of Recombinant Gene Expression Vectors

Compositions of antigen-encoding polynucleotide preparations comprising recombinant gene expression vectors may be placed into a pharmaceutically acceptable suspension, solution or emulsion for administration to mucosa. Suitable mediums include saline and liposomal preparations.

More specifically, pharmaceutically acceptable carriers preferred for use with the gene expression vectors of the invention may include sterile aqueous or non-aqueous solutions, suspensions, and emulsions suitable for ingestion, inhalation, or administration as a suppository to the rectum or vagina. Examples of non-aqueous solvents are propylene glycol, polyethylene glycol, vegetable oils such as olive oil, and certain organic esters such as ethyl oleate. Aqueous carriers include water, alcoholic/aqueous solutions, emulsions or suspensions, including saline and buffered media. Preservatives and other additives may also be present such as, for example, antimicrobials, antioxidants, chelating agents, and inert gases and the like. One skilled in the art will select among these available compounds depending upon the particular mucosal inductor site targeted, i.e., whether for ingestion or inhalation. Further, a composition of antigen-encoding polynucleotide preparations comprising recombinant gene expression vectors may be lyophilized using means well known in the art, for administration by inhalation as an aerosol or subsequent reconstitution and use according to the invention.

Isotonic buffered solution is the preferred medium for maximal uptake of the plasmid gene expression vectors. Further, use of absorption promoters, detergents, and mild chemical irritants is also preferred to enhance transmission of antigen-encoding polynucleotide preparation compositions through the point of entry and into contact with tissue adjacent to or containing a mucosal inductor site. For reference concerning general principles regarding promoters and detergents which have been used with success in mucosal delivery of organic and peptide-based drugs, see Chien, *Novel Drug Delivery Systems,* Ch. 4 (Marcel Dekker, 1992). Specific information concerning known means and principles of nasal drug delivery are discussed in Chien, supra at Ch 5. Examples of suitable nasal absorption promoters are set forth at Ch. 5, Tables 2 and 3; milder agents are preferred. Suitable agents for use in the method of this invention for mucosal/nasal delivery are also described in Chang, et al., *Nasal Drug Delivery,* "Treatise on Controlled Drug Delivery", Ch. 9 and Table 3–4B thereof, (Marcel Dekker, 1992). Suitable agents which are known to enhance absorption of drugs through skin are described in Sloan, *Use of Solubility Parameters from Regular Solution Theory to Describe Partitioning-Driven Processes,* Ch. 5, "Prodrugs: Topical and Ocular Drug Delivery" (Marcel Dekker, 1992), and at places elsewhere in the text.

IV. Methods for In Vivo Use of the Naked Gene Expression Vectors of the Invention A. Definitions The following definitions will be of use in understanding the method of the invention.

a. "Detergents/Absorption Promoters" refers to chemical agents which are presently known in the art to facilitate absorption and transfection of certain small molecules, as well as peptides.

b. "Host" refers to the recipient of the therapy to be practiced according to the invention. The host may be any vertebrate, but will preferably be a mammal. If a mammal, the host will preferably be a human, but may also be a domestic livestock or pet animal.

c. "Target tissue" refers to the mucosal tissue of the host containing a mucosal inductor site in which expression of the polynucleotide is sought.

d. "Mucosa" refers to mucosal tissues of a host wherever they may be located in the body including, but not limited to, respiratory passages (including bronchial passages, lung epithelia and nasal epithelia), genital passages (including vaginal, penile and anal mucosa), urinary passages (e.g., urethra, bladder), the mouth, eyes and vocal cords.

e. "Point of Entry" refers to the site of introduction of the polynucleotide into a host, including immediately adjacent tissue.

f. "TH1 Response(s)" refers to a humoral and cellular immune response that is induced preferentially by antigens that bind to and activate certain APC's; i.e., macrophages and dendritic cells.

g. "Mucosal Inductor Site" refers to a site on the mucosa where uptake of the antigen-encoding polynucleotide preparation is sought, including, but not limited to, Waldeyer's ring, Peyer's patches, gut-associated lympohoid tissues, bronchial-associated lymphoid tissues, nasal-associated lymphoid tissues, genital-associated lymphoid tissues, and tonsils.

h. "Gene Delivery System" refers to an antigen-encoding polynucleotide preparation which comprises the gene sequence for the desired antigen to be encoded along with any promoters and sequences necessary to confer adequate expression.

How the helper T cell subsets are differentially regulated is not completely clear. Factors believed to favor TH1 activation resemble those induced by viral infection and include intracellular pathogens, exposure to IFNg, IFN-a, and IL-2, the presence of APCs and exposure to low doses of antigen.

Factors believed to favor TH2 activation include exposure to IL-4 and IL-10, APC activity on the part of B lymphocytes and high doses of antigen. Active TH1 cells enhance cellular immunity and are therefore of particular value in responding to intracellular infections, while active TH2 cells enhance antibody production and are therefore of value in responding to extracellular infections. However, TH2 cell activity also induces IgE production through the release of IL-4, thus encouraging the formation of IgE-antigen complexes.

For mucosal administration, the means of introduction will vary according to the location of the point of entry. Particularly for immunization to and treatment of respiratory infections, intranasal administration to nasal-associated lymphoid tissues means are most preferred. These means include inhalation of aerosol suspensions or insufflation of the naked gene expression vectors of the invention. Suppositories and topical preparations will also be suitable for introduction to certain mucosa, such as genital, rectal, and ocular sites. Also of particular interest with respect to vaginal delivery of naked gene expression vectors of the invention are vaginal sandwich-type rings and pessaries. Examples of these devices and their use are described in Chien, supra at Ch.9.

The dosage of each gene expression vector to be supplied according to the method of the invention will vary depending on the desired response by the host and the antigenic polynucleotide used. Generally, it is expected that up to 100–200 $\mu$g of polynucleotide can be administered in a single dosage, although as little as about 0.3 $\mu$g of polynucleotide administered through mucosa can induce long lasting immune responses.

For purposes of the invention, however, it is sufficient that the gene expression vectors be supplied at a dosage sufficient to cause expression of the antigenic polypeptide encoded by the polynucleotide sufficient to induce the desired protective immunity as characterized by production of sIgA, for instance as confirmed by lung lavage. Alternative means to confirm the presence and quantity of expressed peptides and/or induced sIgA are well-known to those skilled in the art and will not, therefore, be described in detail. Certain such means are illustrated in the Examples provided below; generally, they include immunoassays (such as enzyme-linked immunosorbent assays), PCR techniques, and immunohistological analyses performed according to techniques which are well known in the art. Dosages of the administered polynucleotides can be adjusted to achieve the desired level of expression based on information provided by these detection and quantification means as well as in vivo clinical signs known to practitioners skilled in the clinical arts.

The desired antigens to be delivered by the methods of the instant invention include, but are not limited to antigens from Human Papalloma Virus, Herpes Simplex Virus, Human Immunodeficiency Virus, Helicobacter Pylorii and *Chlamydia trachomatis*. Examples of antigens from these vectors include but are not limited to Human Papilloma Virus major viral capsid protein L1, Herpes Simplex Virus immediate early protein ICP 27, Human Immunodefieiency Virus envelope, gag, nef, or tat proteins, Helicobacter Pylorii urease protein, *Chlamydia trachomatis* major outer membrane protein Those of ordinary skill in the art will be familiar with the course of dosing employed in vaccination and immunotherapy protocols (i.e., priming, booster and maintenance dosing), which course will be suitable for use in the method of the invention. Generally, it can be expected that doses of less than about 50 μg immunostimulatory polynucleotide, and even less than about 10 μg, will be suitable for priming, booster and maintenance doses in humans. Alternatively, the priming dose of antigen-encoding polynucleotide may be followed by booster and/or maintenance doses of antigen.

Examples illustrating aspects of the invention are provided below. They should be regarded as illustrating rather than limiting the invention, which is defined by the appended claims. Conventional abbreviations (e.g., "ml" for milliliters) are used throughout the Examples.

EXAMPLE 1

SFV particle preparation and Activation:

A recombinant alphavirus vector system which expresses the lac Z gene (β-galactosidase) was obtained from Dr. Peter Liljestrom (1, 2), and defective alphavirus particles were activated by the following protocol (Helper2/SFV-LacZ $10^7$/ml or Helper 2/SFV NP $10^7$/ml as control). One volume of virus stock to 1/20 volume of Chymotrypsin 10 mg/ml (in PBS with Ca/Mg) and 1/50 volume of CaCl2 (50 mM). This was allowed to incubate at room temperature for thirty minutes and then put on ice with a 1/2 volume of Aprotinin at 2 mg/ml was added. This was kept on ice and used within one hour.

Treatment Groups and inoculation procedures:

Three groups of 5 Balb-C mice each (SPF female, 6 week, Charles River) were bled via the retro-orbital venous plexus, and then inoculated with $10^6$ virion particles (Helper2/SFV-LacZ $10^7$/ml)via intratracheal, intranasal or intravenous routes. For histological staining, there was a group of two animals inoculated via intratracheally with Helper2/SFV-LacZ $10^7$/ml. There was also a control group administered Helper 2/SFV NP $10^7$/ml intratracheally. All animals were anesthetized with a cocktail of ketamine (22 mg/kg), xylazine (2.5 mg/kg) and acepromazine 0.75 mg/kg) prior to inoculation.

Intratracheal inoculations were performed by making a small medial cut through the skin at the ventral site of the neck. Salivary glands were teased apart using blunt dissection to expose the trachea. With the trachea visualized, a 30.5 gauge needle with a 1 cc tuberculin syringe attached was placed through the rings of the trachea toward the bronchi. 100 μl of the above virion particles were injected into the lung. Intranasal installation consisted of placing 50 μl of virion particles onto one the nares. Once this was taken into the nasal passages by inhalation, the other side was inoculated in the same manner. Intravenous inoculation was perform using a 30.5 gauge needle with 100 μl of the above virion particles inserted into the tail vein.

Specimen Collection:

Blood was collected from the retro-orbital venous plexus at day 0, 14, and 28, using a microcapillary tube. The blood was allowed to sit at room temperature for 2–4 hours to clot, it was then spun in a IEC Centra MP4R centrifuge at 6,000 RPM for six minutes. The supernatant (serum) was then removed and stored at −20 until ELISA assays were run.

Lung lavages at week 4 were performed by the following method. Mice were killed by carbon dioxide asphyxiation. The ventrum was skinned and the mesentery removed which exposed the liver. The liver is moved aside to visualize the diaphragm. The diaphragm was opened and then the rib cages were cut bi-laterally up through the sternum. This section was lifted up over the mouse's head, leaving the trachea exposed. A transverse cut of the trachea is made approximately 2 cm above the bronchus. A blunt 24 gauge needle is inserted 0.5 cm into the trachea and tied in place with surgical thread. One ml of BBS (89 mM boric acid, 90 mM NaCL: pH.=8.3 [NaOH]) is slowly introduced into the lungs using a 1 ml tuberculin syringe attached to the blunt needle and then the volume is slowly withdrawn. The solution is centrifuged to produce a cellular (particulate) and a supernatant component. Recovered volumes are normally in the range 0.85 to 0.95 ml. This was stored at −20° C. until ELISAs were run.

The treatment group used for histological purposes were killed by carbon dioxide asphyxiation on day two. Their lungs were fixed in paraformaldehyde for thirty minutes, the tissue was then incubated overnight at 4° C. in mix of PBS+2 mM $MgCl_2$+30% sucrose. Lung tissue was cryosectioned and placed on gelatinized slides. The slides were then fixed and stained for beta-galactosidase protein as previously described (D. L. Turner, et al., *Nature*, 328(6126):131–6, 1987; and J. Price, et al., *Proc. Natl. Acad. Sci. USA*, 84(1):156–60, 1987).

Enzyme-linked immunosorbent assay (ELISA)

ELISA assays were performed on samples using 96 well microtiter plates coated with 50 μl of 5 mg. β-galactosidase protein (Calbiochem) per ml BBS (89 mM boric acid, 90 mM NaCL: pH.=8.3 [NaOH]). The β-galactosidase protein had been previously re-suspended to a concentration of 1 mg/ml with PBS supplemented with 5 mg/ml bovine serum albumin (United States Biochemical, Cleveland, Ohio). These plates were incubated overnight at 4° C. The plates were dried by pounding on a stack of paper towels and blocked with 150 μl BB (BBS as above with 1% bovine serum albumin (United States Biochemical) added. After the plates sat at room temperature for 2 hours, eight two-fold dilutions of sample sera in BB were pipetted into the microtiter plates (50 μl per well). Dilutions were performed as follows: Serum IgG and IgA- 1:10 to 1:5120, lavage IgG and IgA- 1:1 to 1:128. These incubated overnight at 4° C. Plates were washed 5–6 times with BBS plus 0.05% Tween and dried. Either alkaline phosphatase conjugated goat anti-mouse IgG (Jackson Labs) at 1:2000 dilution or goat anti-mouse IgA (Zymed) at 1:1000 dilution in BB were added (50 μl per well). Plates were incubated for two hours at room temperature. They were then washed and dried as described above and the substrate buffer (1 mg/ml p-nitrophenol phosphate, 50 mM Na-bicarbonate buffer, pH.=9.8, 1 mM $MgCl_2$) was added. Plates were incubated at room temperature for one hour. A Dynatech MR5000 ELISA plate reader with a 405 nm wavelength (Dynatech Laboratories, Chantilly, Va.) which was hooked up to a Macintosh classic 2 (immunosoft software package) was used to read the plates. Background signal was defined using control serum, with positive titer identified at >2.5× background. For lavage samples, $OD_{405}$ was reported using the 1:2 dilution, with positive signal defined as 2.5× background.

The results of the lung lavage studies showed that intranasal inoculation results in high levels of both IgG and IgA, hallmarks of the induction of a mucosal immune response. On the other hand both intratracheal and intravascular inoculation resulted in a systemic immune response, but did not induce mucosal immunity. However, one mouse treated via intratracheal inoculation did develop pulmonary IgA, which is consistent with reflux nasal inoculation. In general it was found that intranasal inoculation produced secreted mucosal IgA, but not systemic IgA; whereas the other treatment routes resulted in systemic IgA, but not mucosal IgA, showing that polynucleotide vaccine antigens must be expressed in mucosal tissues adjacent to mucosal associated lymphoid tissue, such as is found at the base of the nares in mice.

The examples clearly demonstrate that the response of mucosal tissues to genetic vaccination is affected by the route of administration and hence the site of antigen expression. Gene delivery with antigen expression in skin, muscle, or the respiratory tissues of fowl can elicit robust, protective systemic immunity which is mediated by both humoral and cellular effectors (Fynan, Webster et al. 1993; Ulmer, Donnelly et al. 1993; Zhou, Berglund et al. 1994). This systemic immunity is similar to that observed after recovery from infection, but lacks the secretory IgA responses which are typically observed after infection via mucosal surfaces, and which are a hallmark of mucosal immunity.

Figure 3A:
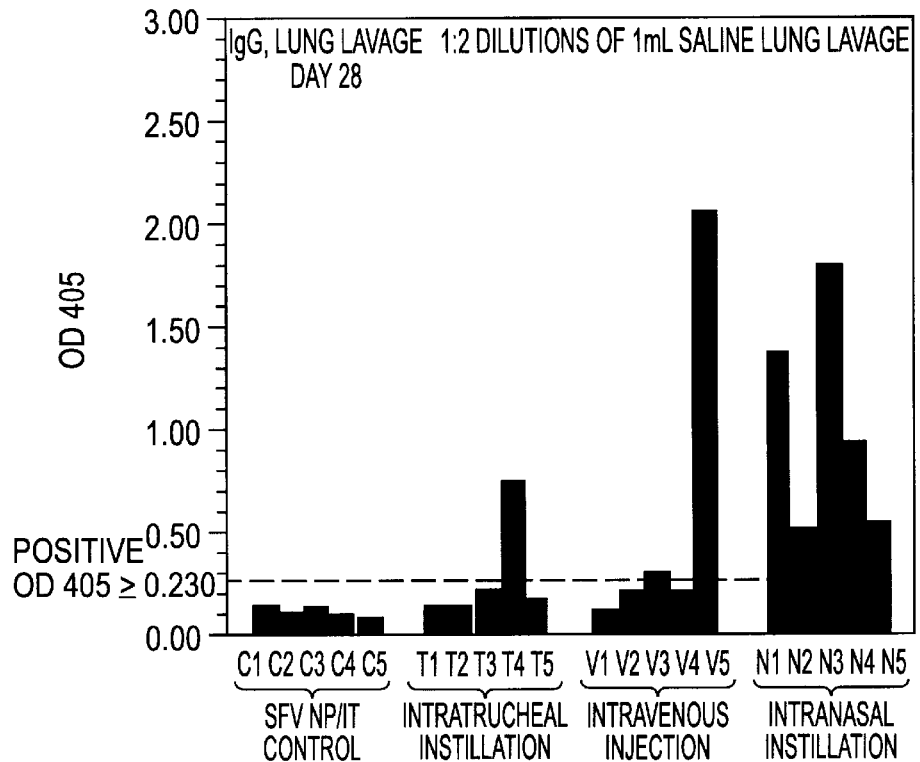
FIGS. 3A and 3B: ELISA analysis of IgG (FIG. 3A) and IgA (FIG. 3B) present in lung lavage fluid obtained at 28 days from mice immunized with recombinant SFV particles. Groups of five female SPF Balb-C mice were immunized with either a control expression vector (Helper 2/SFV-NP) via intratracheal administration (C1–C5), or via intratracheal (T1–T5), intravenous (V1–V5) or intranasal (N1–N5) administration of SFV particles which confer expression of the test antigen β-galatosidase (Helper2/SFV-LacZ). Data reflect lavage fluid diluted 1:2, and positive response was defined as 2.5 times the average signal obtained with control lavage fluid. Variable yield of lavage fluid introduced significant variation in dilution factor, and hence the data is plotted as the yield of reaction product ($OD_{405}$) rather than titer.
Figure 3B:
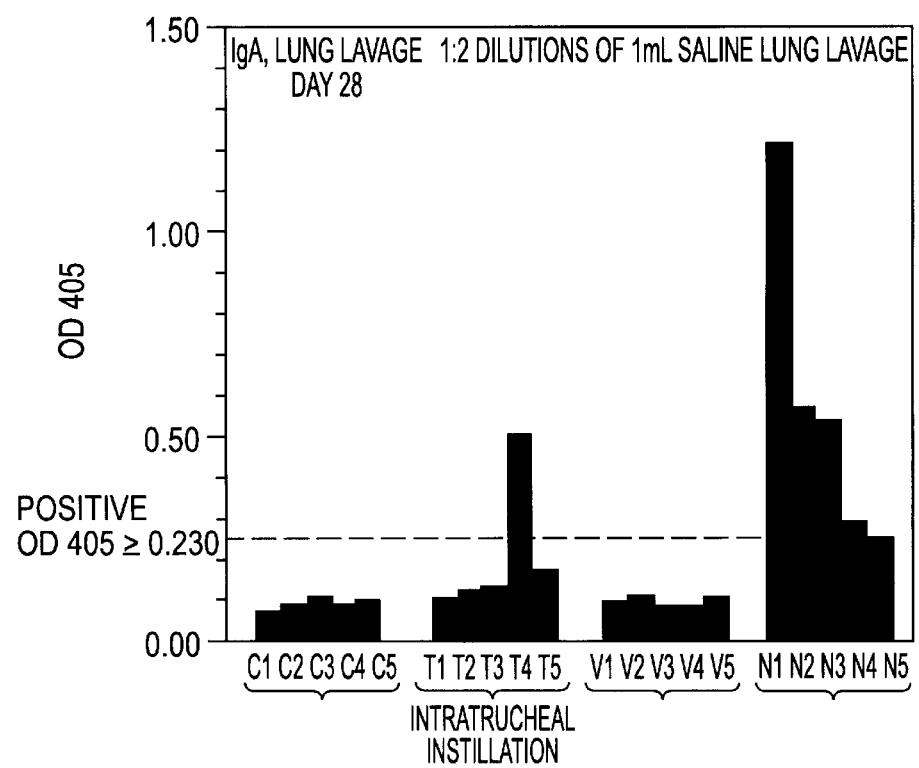

FIGS. 3A and 3B summarize mucosal immune responses associated with intravascular, intratracheal and intranasal transduction and expression of a test antigen, and FIGS. 1A, 1B, 2A and 2B summarize data on corresponding levels of serum immnoglobulins. This data demonstrates the different patterns of immune response predicted by current theory, and supports the hypothesis that antigen expression and/or presentation within mucosal inductor tissues results in a more effective and broad-based mucosal immune response than that associated with expression or presentation within mucosal effector tissues. These results are particularly intriguing in light of studies which demonstrate that mucosal and systemic immune responses can be differentially regulated, so that antigen presented at mucosa can elicit a response in one compartment and anergy in the other (Fujihashi, McGhee et al. 1996). We conclude from these observations that the development of effective genetic or recombinant viral vaccines will be greatly facilitated by incorporating treatment modalities or targeting functionality which will result in antigen expression either within mucosal inductor tissues or epithelial cells overlying such tissues, where antigens can be sampled, processed and delivered by dendritic cells to responsive T and B cells. Administration of gene expression vectors to nonspecific mucosal effector tissues may result in responses which include anergy and/or local but not generalized mucosal immunity, and that such non-targeted patterns of mucosal transduction or transfection may result in systemic but not mucosal immunity.

The invention having been fully described, other embodiments and modifications of the invention may be apparent to those of ordinary skill in the art. All such embodiments and modifications are within the scope of the invention, which is defined by the appended claims.

What is claimed is:

1. A method for inducing a mucosal immune response in a host comprising locally administering to said host an antigen-encoding polynucleotide preparation, whereby administration of said polynucleotide preparation is specifically targeted to mucosal inductor sites.

2. The method of claim 1, wherein said host is a mammal.

3. The method of claim 2, wherein said mammal is a human.

4. The method of claim 1, wherein said antigen-encoding polynucleotide preparation is a viral vector.

5. The method of claim 4, wherein said viral vector contains heterologous regions which encode for epitopic regions of at least one immunogenic protein.

6. The method of claim 5, wherein said immunogenic protein is encoded by a virus selected from the group consisting of Human Papalloma Virus, Herpes Simplex Virus, and Human Immunodeficiency Virus.

7. The method of claim 6, wherein said virus is Human Papalloma Virus.

8. The method of claim 5, wherein said immunogenic protein is the Human Papilloma Virus major viral capsid protein L1.

9. The method of claim 6, wherein said virus is Herpes Simplex Virus.

10. The method of claim 5, wherein said immunogenic protein is the Herpes Simplex Virus immediate early protein ICP 27.

11. The method of claim 6, wherein said virus is Human Immunodeficiency Virus.

12. The method of claim 5, wherein said immunogenic protein is the all or part of the Human Immunodefieiency Virus envelope, gag, nef, or tat proteins.

13. The method of claim 5, wherein said viral vector includes a recombinant alphavirus vector system.

14. The method of claim 1, wherein said antigen-encoding polynucleotide preparation is derived from a prokaryote.

15. The method of claim 14, wherein said prokaryote contains heterologous genetic regions which encode for epitopic regions of at least one immunogenic protein.

16. The method of claim 14, wherein said prokaryote is selected from the group consisting of Helicobacter Pylorii and *Chlamydia trachomatis*.

17. The method of claim 15, wherein said immunogenic protein is all or part of the Helicobacter Pylorii urease protein.

18. The method of claim 15, wherin said immunogenic protein is all or part of the *Chlamydia trachomatis* major outer membrane protein.

19. The method of claim 1, wherein said mucosal inductor sites are selected from the group consisting of Waldeyer's ring, Peyer's patches, gut-associated lymphoid tissues, bronchial associated lymphoid tissues, nasal-associated lymphoid tissues, genital-associated lymphoid tissues, and tonsils.

20. A method for polynucleotide delivery to the mucosal tissue of a host comprising locally administering to said host an antigen-encoding polynucleotide preparation, whereby administration of said polynucleotide preparation is specifically targeted to mucosal inductor sites.

21. The method of claim 20, wherein said host is a mammal.

22. The method of claim 21, wherein said mammal is a human.

23. The method of claim 20, wherein said antigen-encoding polynucleotide preparation is a viral vector.

24. The method of claim 23, wherein said viral vector contains heterologous regions which encode for epitopic regions of at least one immunogenic protein.

25. The method of claim 24, wherein said immunogenic protein is encoded by a virus selected from the group consisting of Human Papalloma Virus, Herpes Simplex Virus, and Human Immunodeficiency Virus.

26. The method of claim 25, wherein said virus is Human Papalloma Virus.

27. The method of claim 24, wherein said immunogenic protein is the Human Papilloma Virus major viral capsid protein L1.

28. The method of claim 25, wherein said virus is Herpes Simplex Virus.

29. The method of claim 24, wherein said immunogenic protein is the Herpes Simplex Virus immediate early protein ICP 27.

30. The method of claim 25, wherein said virus is Human Immunodeficiency Virus.

31. The method of claim 24, wherein said immunogenic protein is the all or part of the Human Immunodefieiency Virus envelope, gag, nef, or tat proteins.

32. The method of claim 1, wherein said antigen-encoding polynucleotide preparation is derived from a prokaryote.

33. The method of claim 32, wherein said prokaryote contains heterologous genetic regions which encode for epitopic regions of at least one immunogenic protein.

34. The method of claim 32, wherein said prokaryote is selected from the group consisting of Helicobacter Pylorii and *Chlamydia trachomatis*.

35. The method of claim 33, wherein said immunogenic protein is all or part of the Helicobacter Pylorii urease protein.

36. The method of claim 33, wherin said immunogenic protein is all or part of the *Chlamydia trachomatis* major outer membrane protein.

37. The method of claim 23, wherein said viral vector includes a recombinant alphavirus vector system.

38. The method of claim 20, wherein said mucosal inductor sites are selected from the group consisting of Waldeyer's ring, Peyer's patches, gut-associated lymphoid tissues, bronchial associated lymphoid tissues, nasal-associated lymphoid tissues, genital-associated lymphoid tissues, and tonsils.

* * * * *